US008859835B2

(12) United States Patent
Clem et al.

(10) Patent No.: US 8,859,835 B2
(45) Date of Patent: Oct. 14, 2014

(54) REGENERATION OF METAL-CONTAINING CATALYSTS

(75) Inventors: Kenneth R. Clem, Humble, TX (US);
Larry L. Iaccino, Seabrook, TX (US);
Mobae Afeworki, Phillipsburg, NJ (US);
Juan D. Henao, Lebanon, NJ (US);
Neeraj Sangar, League City, TX (US);
Xiaobo Zheng, Houston, TX (US);
Lorenzo C. DeCaul, Langhorne, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 205 days.

(21) Appl. No.: 13/218,520

(22) Filed: Aug. 26, 2011

(65) Prior Publication Data
US 2012/0083637 A1   Apr. 5, 2012

Related U.S. Application Data

(60) Provisional application No. 61/388,401, filed on Sep. 30, 2010.

(51) Int. Cl.
*C07C 15/00* (2006.01)
(52) U.S. Cl.
USPC ........... 585/415; 585/319; 585/322; 585/407; 585/417; 502/34; 502/177; 502/305; 502/325; 502/326
(58) Field of Classification Search
USPC ......................................................... 585/415
See application file for complete search history.

(56) References Cited

U.S. PATENT DOCUMENTS

| 4,431,515 | A | 2/1984 | Myers et al. |
| 4,656,148 | A | 4/1987 | Bühler et al. |
| 5,393,717 | A | 2/1995 | Apelian et al. |
| 6,254,665 | B1 | 7/2001 | Matsushita et al. |
| 6,632,765 | B1 * | 10/2003 | Chen ............................. 502/53 |
| 6,913,687 | B2 | 7/2005 | Mayes |
| 7,589,246 | B2 | 9/2009 | Iaccino et al. |
| 2007/0129587 | A1 | 6/2007 | Iaccino et al. |
| 2007/0224098 | A1 | 9/2007 | Miller |
| 2007/0249879 | A1 | 10/2007 | Iaccino et al. |
| 2008/0249342 | A1 | 10/2008 | Iaccino et al. |
| 2009/0030253 | A1 * | 1/2009 | Xu et al. ....................... 585/417 |
| 2009/0305869 | A1 | 12/2009 | Henkelmann et al. |

FOREIGN PATENT DOCUMENTS

| CN | 101402050 A | 4/2009 |
| EP | 2 072 123 | 6/2009 |
| WO | 2009/076005 | 6/2009 |

OTHER PUBLICATIONS

Ranges of Syngas Compositions Across Different Gasifier Type, and Feedstock Produced by the Gasification of Coal Feedstocks, Aug. 13, 2010, National Energy Technology Laboratory, http://www.netl.doe.gov/technologies/coalpower/gasification/gasifipedia/4-gasifiers/4-3_syngas-table2.html.*
CN 101402050A English Translation Apr. 8, 2009.*

(Continued)

*Primary Examiner* — In Suk Bullock
*Assistant Examiner* — Philip Louie
(74) *Attorney, Agent, or Firm* — Catherine L. Bell; Amanda K. Jenkins

(57) ABSTRACT

In a process for the regeneration of a coked metal-containing catalyst, the coked catalyst is contacted in a regeneration zone with an atmosphere which contains carbon dioxide and carbon monoxide at a temperature of at least 400° C.

19 Claims, 7 Drawing Sheets

(56) References Cited

OTHER PUBLICATIONS http://www.netl.doe.gov/technologies/coalpower/gasification/gasifipedia/syngas-composition.html, 2013.
http://www.netl.doe.gov/technologies/coalpower/gasification/gasifipedia/syngas-composition-igcc.html, 2013.
Gong, Lihong et al., "*Study on the regeneration of the Ni-based catalyst for the transformation of natural gas for producing syngas-Regeneration of catalyst deactivated by carbon deposition*," Journal of Molecular Catalysis, vol. 16, No. 6, pp. 423-428, Dec. 2002, Abstract Only.
Shetian, Liu et al., "*Unique promotion effect of CO and $CO_2$ on the catalytic stability for benzene and naphthalene production from methane on Mo/HZSM-5 catalysts*," Chem. Commun., pp. 1217-1218 (Jan. 1, 1998).

* cited by examiner

REGENERATION OF METAL-CONTAINING CATALYSTS

PRIORITY CLAIM

This application claims the benefit of U.S. Provisional Application No. 61/388,401, filed Sep. 30, 2010, the entirety of which is incorporated by reference.

FIELD

This invention relates to a regeneration of metal-containing catalysts and particularly, but not exclusively, metal-containing catalysts employed in the conversion of methane to aromatic hydrocarbons.

BACKGROUND

Aromatic hydrocarbons, particularly benzene, toluene, ethylbenzene and xylenes, are important commodity chemicals in the petrochemical industry. Currently, aromatics are most frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, such as aromatics, is an attractive method of upgrading natural gas, providing the attendant technical difficulties can be overcome.

A large majority of the processes currently proposed for converting methane to liquid hydrocarbons involve initial conversion of the methane to synthesis gas, a blend of $H_2$ and CO. However, production of synthesis gas is capital and energy intensive and hence routes that do not require synthesis gas generation are preferred.

A potentially attractive route for upgrading methane directly into higher hydrocarbons, particularly ethylene, benzene and naphthalene, is dehydroaromatization or reductive coupling. This process typically involves contacting the methane with a catalyst comprising a metal or metal carbide, such as molybdenum carbide, supported on a zeolite, such as ZSM-5, at high temperature, such as about 600° C. to about 1000° C., and low pressure, typically about 100 kPa to about 600 kPa. However, these conditions also favor build-up of carbon and other non-volatile materials, collectively referred to as "coke", on the catalyst resulting in rapid loss of activity and potentially undesirable selectivity shifts, as well as loss of valuable feedstock. As a result, the catalyst is required to undergo frequent transfer, often every few minutes, between a reaction cycle, in which the catalyst effects methane conversion and accumulates coke, and a regeneration cycle, in which the coke is removed from the catalyst.

Thus the successful application of reductive coupling to produce aromatics on a commercial scale requires the development of a regeneration process that is not only effective at removing coke but also has minimal adverse affect on the metal-containing catalyst.

Currently, most methane dehydroaromatization processes propose the use of regeneration in the presence of an oxygen-containing gas since this is known to be very effective at coke removal. For example, U.S. Patent Application Publication No. 2007/0249879 discloses a process for converting methane to aromatic hydrocarbons over a catalyst comprising molybdenum, tungsten, zinc and/or rhenium in metallic or carbide form on a support, such as, ZSM-5, in which the coked catalyst is regenerated in an oxygen containing gas which may also contain carbon dioxide and/or nitrogen such that the oxygen concentration of the regeneration gas is from about 2 wt % to about 10 wt %.

Likewise, WO 2009/076005 teach a method of dehydroaromatizing methane with a catalyst comprising montmorillonite, a non-zeolitic molybdenum compound such as molybdenum oxide, and at least one zeolite that comprises at least one element selected from Cr, Mo, Fe, Co, Ni, Zn, Re, Ru, Rh, Pd, Os, Ir, Pt, W, and V. After deactivation, it is taught that the deactivated catalyst is re-activated via oxidation by exposure to air or some other suitable $O_2$-containing gas stream or a less severe regeneration such as using $H_2$ or a mixture of $CO/CO_2$ to achieve a low oxygen concentration. A preferred mixture of $CO/CO_2$ has a volumetric ratio of 1:1.

However, the above approaches have problems. For example, depending on the composition of the catalyst, regeneration in an oxidative environment can lead to a variety of unwanted ancillary results. For example, the metal on the catalyst may be converted from a catalytically active elemental or carburized state to a less active oxidized state. Also, following regeneration, the catalyst may exhibit enhanced activity for coke deposition and related hydrogen generation. In particular, with a molybdenum-containing catalyst on an aluminosilicate support, it is found that oxidative regeneration can cause rapid and permanent deactivation of the catalyst, due to effect such as production of aluminum molybdate and metal agglomeration.

To avoid this problem it has been proposed in, for example, U.S. Patent Application Publication No. 2008/0249342, regenerating a coked metal-containing methane dehydroaromatization catalyst by heating in a hydrogen-containing gas at a temperature of 700° C. to about 1200° C. so as to convert at least part of the carbonaceous material thereon to methane. However, although hydrogen regeneration is generally effective at removing freshly deposited coke while preserving metal dispersion, we have found that regeneration with hydrogen alone leads to a gradual build-up of graphitic coke on the exterior of the crystals of the zeolite support. This build-up eventually causes loss of access to the active sites of the catalyst and permanent deactivation of the catalyst.

In accordance with the present invention, it has now been found that regeneration in the presence of $CO_x$ (CO and $CO_2$) is an effective method of removing graphitic and other hard to remove coke, while preserving metal dispersion. The $CO_x$ regeneration can be used alone or in combination with hydrogen regeneration. While this method is particularly effective in the regeneration of metal-containing methane dehydroaromatization catalysts, such as molybdenum-containing ZSM-5, it is believed to be equally applicable to other metal-containing catalysts, such as cobalt, tungsten, zinc, rhenium, platinum, palladium and mixtures thereof.

U.S. Patent Application Publication No. 2009/0305869 discloses a method of regenerating a ruthenium catalyst suitable for hydrogenation of aromatics, which comprises flushing the catalyst with inert gas in a regeneration step until the original activity or part of the original activity has been attained. The inert gas is selected from among nitrogen, carbon dioxide, helium, argon, neon and mixtures thereof and the flushing is carried out at a temperature of from 10 to 350° C.

SUMMARY

In one aspect, the invention resides in a process for the regeneration of a coked metal-containing catalyst, the process comprising contacting the coked metal-containing catalyst in a regeneration zone with an atmosphere which contains carbon monoxide and carbon dioxide in a ratio, based on partial pressures, of at least 2.3:1, and less than 100 ppm of molecular oxygen, at a temperature of at least 400° C.

Conveniently, the ratio of the partial pressure of carbon monoxide to the partial pressure of carbon dioxide in the regeneration zone is in the range of 2.3:1 to 100:1, and more preferably at least 10:1. Generally, the partial pressure of carbon dioxide in the regeneration zone is less than or equal 40 psia (276 kPaa), such as between about 0.1 and about 40 psia (0.7 to 276 kPaa).

Conveniently, said contacting is for a time of less than 120 minutes, such as for a time between about 0.1 and about 60 minutes.

Conveniently, said temperature is between about 400° C. and about 1200° C., such as between about 600° C. and about 800° C.

In one embodiment, the process further comprises contacting the coked metal-containing catalyst in a regeneration zone with an atmosphere which contains hydrogen at a temperature of at least 400° C., either simultaneously or consecutively with said contacting with said atmosphere containing carbon dioxide and carbon monoxide.

Conveniently, the metal of said catalyst is selected from molybdenum, tungsten, cobalt, zinc, rhenium, platinum, palladium and mixtures thereof, especially molybdenum in a carbide form.

Conveniently, the catalyst comprises a support selected from ZSM-5, silica, alumina, zirconia, titania, barium aluminate and mixtures thereof.

In a further aspect, the invention resides in a process for converting methane to higher hydrocarbons including aromatic hydrocarbons, the process comprising:

(a) supplying a feedstock comprising methane to a reaction zone comprising a metal-containing catalyst;

(b) operating said reaction zone under reaction conditions effective to convert at least a portion of said methane to said higher hydrocarbon(s) and to deposit carbonaceous material on the metal-containing catalyst causing deactivation of the catalyst;

(c) transferring at least a portion of said deactivated metal-containing catalyst to a regeneration zone;

(d) contacting said portion of said deactivated metal-containing catalyst in said regeneration zone with an atmosphere which contains carbon monoxide and carbon dioxide, preferably in a ratio, based on partial pressures, of at least 2.3:1, more preferably in the range of 2.3:1 to 100:1, and still more preferably from about 10:1 to 100:1, in the substantial absence of molecular oxygen, such as less than 100 ppm, preferably less than 10 ppm, still more preferably less than 1 ppm, at a temperature of at least 400° C. so as to remove at least part of the carbonaceous material on the catalyst and regenerate the catalyst; and (e) returning at least part of the regenerated catalyst to said reaction zone.

Conveniently, the partial pressure of carbon dioxide in the regeneration zone is less than or equal 5 psia (34 kPaa), such as between about 0.1 and about 5 psia (0.7 to 34 kPaa). Generally, the partial pressure of carbon dioxide in the regeneration zone is less than or equal 5 psia (34 kPaa), such as between about 0.1 and about 3 psia (0.7 to 21 kPaa).

Conveniently, said contacting is for a time of less than 15 minutes, such as for a time between about 0.1 and about 10 minutes.

Conveniently, the process further comprises:

(f) contacting at least a portion of said deactivated metal-containing catalyst in a regeneration zone with an atmosphere which contains hydrogen at a temperature of at least 400° C. so as to remove at least part of the carbonaceous material on the catalyst and regenerate the catalyst.

In one embodiment, the catalyst is cycled between said operating (a) and at least one of said contacting (d) or said contacting (f) such that the catalyst undergoes said contacting (f) about 2 to about 100 times for each time the catalyst undergoes said contacting (d).

In another embodiment, the catalyst is cycled between said operating (a) and at least one of said contacting (d) or said contacting (f) such that, each time the catalyst undergoes said contacting (d), the catalyst also undergoes said contacting (f) before being returned to said reaction zone.

DETAILED DESCRIPTION OF THE EMBODIMENTS

Figure 1A:
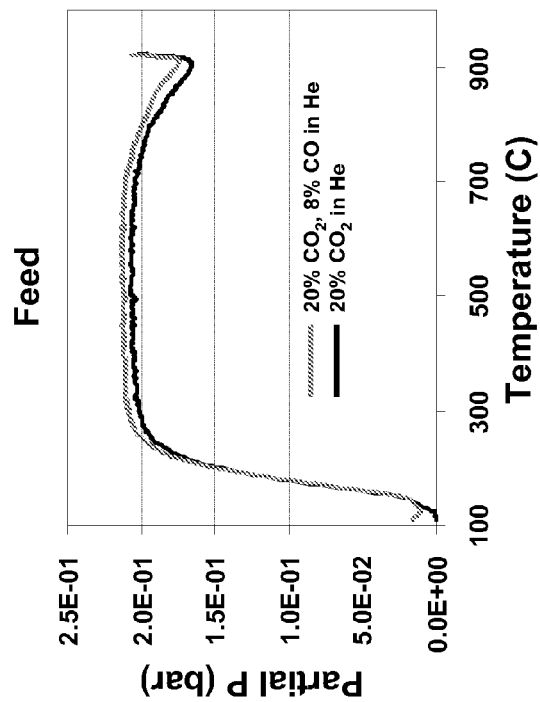
FIGS. 1(a) and 1(b) are graphs of temperature against regeneration feed partial pressure and regeneration product partial pressure, respectively, during heating of a coked Mo/ZSM-5 catalyst in (a) a $CO_2$/helium atmosphere and (b) a $CO_2$/CO/helium atmosphere according to the process of Example 1.

The terms "coke" and "carbonaceous material" are used herein interchangeably to mean the low hydrogen content (typically with a H/C molar ratio of less than 0.8, such as less than 0.5), carbon-containing materials which are produced as the by-products of catalytic reactions and which are essentially non-volatile solids at reaction conditions. These may include crystalline graphite, graphitic sheets, graphitic fragments, amorphous carbon, or other carbon containing structures which are essentially non-volatile solids at reaction conditions.

The term "coked metal-containing catalyst" means a catalyst composition which comprises a catalytically active metal and which contains coke as a result of use of the catalyst composition in a catalytic reaction such that the activity of the catalyst composition for continued use in the reaction is impaired.

The terms "regenerating" and "regeneration" are used herein to refer to a process by which carbonaceous material on a coked metal-containing catalyst is removed and/or rendered less detrimental to the use of the catalyst composition in the desired catalytic reaction.

Described herein is a process for regenerating a coked metal-containing catalyst, in which the coked catalyst is contacted with an atmosphere containing carbon dioxide and carbon monoxide at a temperature of at least 400° C. Although the present process has utility with any metal-containing catalyst whose activity has been impaired as a result of use in any catalytic reaction, the process is particularly intended for regenerating a metal-containing catalyst used in the dehydrocyclization of methane to higher hydrocarbons including aromatic hydrocarbons. The invention will therefore now be more particularly described with reference to a methane dehydrocyclization reaction.

Feedstock

Any methane-containing feedstock can be used in the present methane dehydrocyclization reaction but in general the present process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can of course be converted to desired aromatics products in the dehydrocyclization step. In addition, as will be discussed below, carbon dioxide can also be converted to useful aromatics products either directly in the dehydrocyclization step or indirectly through conversion to methane and/or ethane in a subsequent hydrogen rejection step.

Nitrogen and/or sulfur impurities are also typically present in methane-containing streams and may be removed, or reduced to low levels, prior to use of the streams in the process of the invention. In an embodiment, the feed to the dehydrocyclization step contains less than 100 ppm, for example less than 10 ppm, such as less than 1 ppm each of nitrogen and sulfur compounds.

In addition to methane, the feed to the dehydrocyclization step may contain at least one of hydrogen, water, oxygen, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydrocyclization step contains carbon dioxide and comprises about 90 to about 99.9 mol %, such as about 97 to about 99 mol % methane and about 0.1 to about 10 mol %, such as about 1 to about 3 mol % $CO_2$. In another embodiment, the feed to the dehydrocyclization step contains carbon monoxide and comprises about 80 to about 99.9 mol %, such as about 94 to about 99 mol % methane and about 0.1 to about 20 mol %, such as about 1 to about 6 mol % CO. In a further embodiment, the feed to the dehydrocyclization step contains steam and comprises about 90 to about 99.9 mol %, such as about 97 to about 99 mol % methane and about 0.1 to about 10 mol %, such as about 1 to about 5 mol % steam. In yet a further embodiment, the feed to the dehydrocyclization step contains hydrogen and comprises about 80 to about 99.9 mol %, such as about 95 to about 99 mol % methane and about 0.1 to about 20 mol %, such as about 1 to about 5 mol % hydrogen.

The feed to the dehydrocyclization step can also contain higher hydrocarbons than methane, including aromatic hydrocarbons. Such higher hydrocarbons can be recycled from a subsequent hydrogen rejection step, added as separate co-feeds or can be present in the methane stream, such as, for example, when ethane is present in a natural gas feed. Higher hydrocarbons recycled from a subsequent hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3$+ hydrocarbons.

Dehydrocyclization Reaction and Catalyst

In the dehydrocyclization reaction of the present process, the methane containing feedstock is contacted with a particulate metal-containing dehydrocyclization catalyst under conditions, normally non-oxidizing conditions and typically reducing conditions, effective to convert the methane to higher hydrocarbons, including benzene and naphthalene. The principal net reactions involved are as follows:

$$2CH_4 \leftrightarrow C_2H_4 + 2H_2 \quad \text{(Reaction 1)}$$

$$6CH_4 \leftrightarrow C_6H_6 + 9H_2 \quad \text{(Reaction 2)}$$

$$10CH_4 \leftrightarrow C_{10}H_8 + 16H_2 \quad \text{(Reaction 3)}$$

Carbon monoxide and/or dioxide that may be present in the feed improve catalyst activity and stability by facilitating reactions such as:

$$CO_2 + coke \rightarrow 2CO \quad \text{(Reaction 4)}$$

but negatively impact equilibrium by allowing competing net reactions, such as:

$$CO_2 + CH_4 \leftrightarrow CO + 2H_2 \quad \text{(Reaction 5).}$$

Any dehydrocyclization catalyst effective to convert methane to aromatics can be used in the present process, although generally the catalyst will include a metal component, particularly a transition metal or compound thereof, on an inorganic support. Conveniently, the metal component is present in an amount between about 0.1% and about 20%, such as between about 1% and about 10%, by weight of the total catalyst. Generally, the metal will be present in the catalyst in elemental form or as a carbide species.

Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, platinum, copper, silver, gold, zinc, aluminum, gallium, silicon, germanium, indium, tin, lead, bismuth and transuranium metals. Such metal components may be present in elemental form or as metal compounds, such as oxides, carbides, nitrides and/or phosphides, and may be employed alone or in combination.

The inorganic support may be either amorphous or crystalline and in particular may be an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous crystalline material or a mesoporous material. As used herein the term "microporous" refers to pores having a diameter of less than 2 nanometers, whereas the term "mesoporous" refers to pores having a diameter of from 2 to 50 nanometers.

Suitable microporous crystalline materials include silicates, aluminosilicates, titanosilicates, aluminophosphates, metallophosphates, silicoaluminophosphates or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), VFI (e.g., VPI-5), AEL (e.g., SAPO-11), AFI (e.g., ALPO-5) and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50, FSM-16 and SBA-15.

Examples of preferred catalysts include molybdenum, tungsten, zinc, rhenium and compounds and combinations thereof on ZSM-5, silica or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion and physical mixing. In addition, the inorganic support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the support and hinder or enhance access to any internal pore structure of the support.

In some embodiments, a non-catalytic particulate material may be supplied to the dehydrocyclization reaction in addition to the catalytic particulate material. The non-catalytic particulate material may be used as a material to transport energy (heat) into the system and/or to fill space as required providing the required hydrodynamic environment. The non-catalytic particulate material may form particulates without a binder or may be bound with an inorganic binder such as clay, silica, alumina, zirconia, or other metal oxide used to help maintain the physical integrity of the particles. Preferably the particles are of a substantially spherical shape. Examples of suitable non-catalytic particulate material are low surface area silica, alumina, ceramics, and silicon carbide.

The dehydrocyclization step is conducted by contacting the methane-containing feedstock with the particulate dehydrocyclization catalyst in one or more fixed bed, moving bed or fluidized bed reaction zones. Generally, the feedstock is contacted in the or each reaction zone with a moving bed of dehydrocyclization catalyst, wherein the feedstock flows countercurrent to the direction of movement of the dehydrocyclization catalyst. In one embodiment, the or each reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed.

The movement of the dehydrocyclization catalyst in the reaction zone is substantially free of fluidization in the settling bed embodiment. The term "substantially free of fluidization" as used herein means that the average gas flowing velocity in the reactor is lower than the minimum fluidizing velocity. The term "substantially free of fluidization" as used herein also means that the average gas flowing velocity in the reactor is less than 99%, such as less than 95%, typically less than 90%, even less than 80% of the minimum fluidization velocity. Where the or each reaction zone is operated as a settling bed, the particulate catalytic material and/or any particulate non-catalytic material has an average particle size from about 0.1 mm to about 100 mm, such as from about 1 mm to about 5 mm, and for example from about 2 mm to about 4 mm. In some embodiments, at least 90 wt % of the particulate catalytic material and/or at least 90 wt % of the particulate non-catalytic material has a particle size from about 0.1 mm to about 100 mm, such as from about 1 mm to about 5 mm, for example from about 2 mm to about 4 mm.

In an alternative embodiment, the dehydrocyclization reaction is conducted in a plurality of series-connected fluidized bed reactors in which particulate catalyst is cascaded in one direction from one reactor to the next adjacent reactor in the series, while the feed is passed through and between the reactors in the opposite direction. Wherein each reaction zone is operated as a fluidizing bed, the catalytic particulate material and/or any non-catalytic particulate material has an average particle size from about 0.01 mm to about 10 mm, such as from about 0.05 mm to about 1 mm, and for example from about 0.1 mm to about 0.6 mm. In some embodiments, at least 90 wt % of the catalytic particulate material and/or at least 90 wt % of the non-catalytic particulate material have particle size from about 0.01 mm to about 10 mm, such as from about 0.05 to about 1 mm, and for example from about 0.1 to about 0.6 mm.

Typically, the mass ratio of the flowrate of the catalytic particulate material plus any non-catalytic particulate material over the flowrate of the hydrocarbon feedstock in the or each dehydrocyclization reaction zone is from about 1:1 to about 100:1, such as from about 1:1 to about 40:1, for example from about 5:1 to 20:1.

The dehydrocyclization reaction is endothermic and hence the temperature in each dehydrocyclization reaction zone will tend to decrease from a maximum temperature to a minimum temperature as the reaction proceeds. Suitable conditions for the dehydrocyclization step include a maximum temperature of about 700° C. to about 1200° C., such as about 800° C. to about 950° C. and a minimum temperature of about 400° C. to about 800° C., such as about 500° C. to about 700° C. However, as will be discussed below, heat is supplied to the dehydrocyclization reaction to reduce the temperature drop during the reaction and hence in some configurations it is possible to reduce the difference between the maximum and minimum temperatures to essentially zero. Alternatively, by supplying heated catalyst to the dehydrocyclization reaction, it is possible to produce an inverse temperature profile; that is with the process gas outlet reaction temperature being greater than the process gas inlet reaction temperature.

In one embodiment, the countercurrent flow of the feedstock and the particulate dehydrocyclization catalyst is arranged to produce an inverse temperature profile across dehydrocyclization reaction system, such that, despite the endothermic nature of the dehydrocyclization reaction, the difference between the reaction temperature of the gaseous effluent at the outlet from the dehydrocyclization reaction system and the reaction temperature of the methane-containing feed at the inlet to the dehydrocyclization reaction system is at least +10° C., such as at least +50° C., for example at least +100° C., and even at least +150° C.

In any event, since the dehydrocyclization reaction is endothermic, the catalytic particulate material enters the dehydrocyclization reaction system at a first, high temperature, typically about 800° C. to about 1200° C., such as about 900° C. to about 1100° C., and exits the reaction system at a second lower temperature, typically about 500° C. to about 800° C., such as about 600° C. to about 700° C. The total temperature difference of the catalytic particulate material across the reaction zones is at least 100° C.

Other conditions used in the dehydrocyclization reaction generally include a pressure of about 1 kPaa to about 1000 kPaa, such as about 10 to about 500 kPaa, for example about 50 kPaa to about 200 kPaa and a weight hourly space velocity of about 0.01 to about 1000 $hr^{-1}$, such as about 0.1 to about 500 $hr^{-1}$, for example about 1 to about 20 $hr^{-1}$. Conveniently, the dehydrocyclization step is conducted in the absence of $O_2$, preferably less than 100 ppm $O_2$, more preferably less than 10 ppm $O_2$, still more preferably less than 1 ppm $O_2$.

The major components of the effluent from the dehydrocyclization step are hydrogen, benzene, naphthalene, carbon monoxide, ethylene, and unreacted methane. Typically, the effluent contains at least 5 wt %, such as at least 10 wt %, for example at least 20 wt %, conveniently at least 30 wt %, more aromatic rings than the feed.

The benzene and naphthalene are separated from the dehydrocyclization effluent, for example, by solvent extraction followed by fractionation, and can be recovered as a product stream. However, as will be discussed below, at least part of these aromatic components can be submitted to an alkylation step, before or after product recovery, to produce higher value materials, such as xylenes. Moreover, as will be discussed below, the present process utilizes the hydrogen generated as a by-product of the dehydrocyclization reaction and in particular converts at least part of the hydrogen to higher value products.

Catalyst Regeneration

The dehydrocyclization reaction tends to deposit coke on the catalyst and hence, to maintain the activity of the dehydrocyclization catalyst, at least part of the catalyst must be continuously or intermittently regenerated. This is typically achieved by withdrawing a portion of the catalyst from the or each reaction zone, either on an intermittent, or a continuous basis, and transferring the withdrawn catalyst to a separate regeneration zone. In the regeneration zone, the coked dehydrocyclization catalyst is contacted with a gaseous mixture of carbon monoxide and carbon dioxide under conditions effective to remove at least a portion of the carbonaceous material on the catalyst.

Generally, the ratio of the partial pressure of carbon monoxide to the partial pressure of carbon dioxide in the regeneration zone is in a ratio, based on partial pressures, of at least 2.3:1, more preferably in the range of 2.3:1 to 100:1, and still more preferably from about 10:1 to 100:1. In addition, the partial pressure of carbon dioxide in the regeneration zone is generally less than or equal 40 psia (276 kPaa), such as between about 0.1 and about 40 psia (0.7 to 276 kPaa). More particularly, the partial pressure of carbon dioxide in the regeneration zone is less than or equal 5 psia (34 kPaa), such as between about 0.1 and about 3 psia (0.7 to 21 kPaa). Generally, the regeneration gas is substantially free of molecular oxygen (preferably less than 100 ppm $O_2$, more preferably less than 10 ppm $O_2$, still more preferably less than 1 ppm $O_2$) and does not contain significant quantities of methane or other hydrocarbons; typically with the hydrocarbon content being less than 20 mol %, such as less than 10 mol %, for example less than 2 mol %.

Conveniently, the regeneration conditions comprise a temperature of at least 400° C., such as from about 400° C. to about 1200° C., such as from about 600° C. to about 800° C. In some cases, the coked dehydrocyclization catalyst removed from the or each reaction zone will be at a lower temperature than the optimum for regeneration and hence the removed catalyst is initially heated to a desired regeneration temperature by direct and/or indirect contact with combustion gases produced by combustion of a supplemental fuel. The heating is conducted in a heating zone which may be in the same vessel as the regeneration zone or which may be in a separate vessel from the regeneration zone.

By "supplemental source of fuel" is meant that the source fuel is physically separate from the catalyst and hence is not, for example, coke generated on the catalyst as a by-product of the dehydrocyclization reaction. Typically, the supplemental source of fuel comprises a hydrocarbon, such as methane, and in particular a suitable fuel source is the natural gas used as the feedstock to the process. Conveniently, an oxygen-lean atmosphere is maintained in the heating zone so that burning the hydrocarbon fuel to heat the coked catalyst produces synthesis gas, which can then be used to generate additional hydrocarbon product and/or fuel. In addition, in the case of direct heat transfer to the coked catalyst, the use of an oxygen-lean atmosphere inhibits oxidation of metal carbides present in the catalyst and minimizes the average steam partial pressure thereby reducing catalyst hydrothermal aging.

Alternatively, a suitable supplemental fuel source is hydrogen and, in particular, part of the hydrogen generated as a by-product of the dehydrocyclization reaction.

Where the dehydrocyclization catalyst is heated directly, the coked catalyst withdrawn from the reaction zone is conveniently contacted directly with the burning source of fuel in the heating zone. Alternatively, the source of fuel is burned in a separate combustion zone and the combustion gases generated in the combustion zone are fed to the heating zone to heat the catalyst. Alternatively, the dehydrocyclization catalyst can be heated by indirect heat exchange such as, for example, by using the combustion gases to heat an inert medium (gas, liquid, or solid) or a heat transfer surface and then contacting the coked catalyst with the heated inert medium or heat transfer surface.

In one practical embodiment, the heating zone is elongated and the coked catalyst is passed through the heating zone from an inlet at or adjacent one end of the heating zone to an outlet at or adjacent the other end of the heating zone, with heat being applied to first catalyst portion at a plurality of locations spaced along the length of the heating zone. In this way, the heat input to the catalyst can be distributed along the length of the heating zone thereby minimizing catalyst surface temperatures and internal gradients.

Where the coked catalyst is heated by direct contact with the burning source of fuel in the heating zone, gradual heating of the catalyst can be achieved by supplying substantially all of the supplemental fuel to the inlet end of the heating zone and then supplying the oxygen-containing gas incrementally to said heating zone at said plurality of spaced locations along the length of heating zone. Alternatively, substantially all of the oxygen-containing gas required to burn said supplemental fuel can be supplied to the inlet end of the heating zone and the supplemental fuel supplied incrementally to the heating zone at said plurality of spaced locations.

Where the coked catalyst portion is heated by direct contact with hot combustion gases generated in a separate combustion zone, gradual heating of the catalyst can be achieved by supplying the hot combustion gases to said plurality of spaced locations along the length of heating zone.

In one embodiment, the heating zone is a riser and the coked catalyst is passed upwardly through the riser during the reheating step. In practice, the heating zone may include a plurality of risers connected in parallel. Alternatively, said heating zone can include a moving bed of the coked catalyst.

Generally, regeneration is conducted by contacting the coked catalyst with the carbon monoxide/carbon dioxide mixture at the desired regeneration temperature for a time of less than 120 minutes, such as for between about 0.1 and about 60 minutes. More particularly, the coked catalyst is contacted with the carbon monoxide/carbon dioxide mixture at the desired regeneration temperature for a time of less than 15 minutes, such as for between about 0.1 and about 10 minutes. Although the mechanism of the regeneration is not fully understood it is believed that the carbon dioxide present in the regeneration mixture removes coke (CH$_x$) according to the following general reaction:

$$CH_x + CO_2 \leftrightarrow wCO + yH_2 + zH_2O \quad \text{(Reaction 6)}$$

In addition, the presence of carbon monoxide at sufficient partial pressure to maintain carbon activity in the regeneration zone allows the catalytically active metal to be maintained in a reduced state or more preferably a carburized state, for example, in the case of a molybdenum-containing catalyst, in the MoC$_x$ form.

In one embodiment, regeneration is conducted by a combination of the carbon monoxide/carbon dioxide regeneration described above and by contacting the coked catalyst with an atmosphere containing hydrogen at a temperature of at least 400° C., preferably at about 600° C. to about 850° C. This combined regeneration process can be conducted simultaneously, that is by contacting the coked catalyst with an atmosphere containing CO, CO$_2$ and H$_2$, or consecutively, that is by contacting the coked catalyst with an atmosphere containing CO and CO$_2$ prior to and/or after contacting the coked catalyst with an atmosphere containing H$_2$ in the same or different regeneration zones. The combined CO/CO$_2$ and H$_2$ regeneration achieves the advantages of hydrogen regeneration (efficient removal of freshly deposited coke while preserving metal dispersion) without build-up of graphitic coke that can occur with hydrogen regeneration alone.

Where the combined regeneration process is conducted in consecutive steps, a number of different alternative approaches can be adopted, for example:

(a) H$_2$ regeneration can be used as the primary mode of maintaining catalyst activity with an occasional CO/CO$_2$ regeneration being used to remove heavy, difficult to remove (graphitic) coke. The frequency of CO/CO$_2$ regeneration might vary between from every other regeneration to 1 in 10 or even 1 in 100 H$_2$ regenerations.

(b) Each CO/CO$_2$ regeneration can be followed with a H$_2$ regeneration before returning the catalyst from regeneration mode to on-oil operation.

(c) H$_2$ regeneration can be used as the primary mode of maintaining catalyst activity with an occasional CO/CO$_2$ regeneration as in (a) above and with each CO/CO$_2$ regeneration being followed with a H$_2$ regeneration before returning the catalyst from regeneration mode to on-oil operation.

With a combined CO/CO$_2$ and H$_2$ regeneration process, the ratio of the partial pressure of carbon monoxide to the partial pressure of carbon dioxide in the CO/CO$_2$ regeneration gas is preferably at least 2.3:1, more preferably in the range of 2.3:1 to 100:1, and still more preferably from about 10:1 to 100:1, and the partial pressure of carbon dioxide is preferably less than 20 psia (138 kPaa), such as between about 0.1 and about 15 psia (7 to 103 kPaa). Typically, contacting with the CO/CO$_2$ regeneration gas is for a time of less than 20 minutes, such as for between about 0.1 and about 15 minutes, whereas contacting with the H$_2$ regeneration gas is typically for a time greater than 4 minutes, such as for between about 20 and about 60 minutes.

The or each regeneration zone may be a reactor operated as a fluidized bed, an ebulating bed, a settling bed, a riser reactor or a combination thereof. In practice, each regeneration zone may include a plurality of reactors, such as a plurality of riser reactors connected in parallel or a plurality of reactors connected in series such as a riser reactor followed by a settling bed. After regeneration the catalyst is returned to reaction zone.

In an alternative embodiment, and particularly where the dehydrocyclization reaction is conducted in a fixed bed reactor, the regeneration can be conducted without removal of the catalyst from the reaction zone, by temporarily discontinuing the supply of methane-containing feedstock to the reaction zone, heating the reaction zone to the desired regeneration temperature by direct and/or indirect contact with combustion gases produced by combustion of a supplemental fuel, regenerating the particulate catalytic material with a CO/CO$_2$-containing gas alone or in combination with a H$_2$-containing gas, and then re-establishing the supply of methane-containing feedstock to the reaction zone. It is to be appreciated that heating the reaction zone to the regeneration temperature can be effected before the supply of methane-containing feedstock is discontinued.

Catalyst Reheating

Since the dehydrocyclization reaction is endothermic, it is necessary to supply heat to the reaction. In the present process, this is conveniently achieved by withdrawing part of the catalyst from the reaction zone, either on an intermittent or a continuous basis, supplying heat to the catalyst and then returning the heated catalyst back to the reaction zone. Since the hydrogen regeneration step described above also involves heating the catalyst and then recycling the heated regenerated catalyst back to the reaction zone, one possible route for supplying heat to the dehydrocyclization reaction is by means of the regeneration process.

Alternatively, some or all of the heat required to maintain the dehydrocyclization reaction can be supplied by a separate catalyst reheating step. In this embodiment, part of the catalyst withdrawn for the reaction zone is transferred to a separate heating zone, where again the catalyst is heated by direct or indirect contact with hot combustion gases generated by burning a supplemental source of fuel. The heated catalyst is then returned to the reaction zone with or without undergoing hydrogen regeneration.

Catalyst Recarburizing

It will be appreciated that heating the dehydrocyclization catalyst for the purposes of regeneration and/or for heat transfer back the dehydrocyclization reaction may subject the catalyst to high temperature oxidizing conditions, especially where catalyst heating involves direct contact with hot combustion gases. As a result, metals, such as rhenium, tungsten or molybdenum, present in the dehydrocyclization catalyst may be converted during the heating step from their catalytically active elemental or carbide form to an oxide species. Thus, before being returned to the reaction zone, the regenerated and/or reheated catalyst may be transferred to a catalyst treatment zone separate from the regeneration zone, the heating zone and the reaction zone, where the catalyst is contacted with a carburizing gas containing at least one hydrocarbon selected from methane, ethane, propane, butane, isobutene, hexane, benzene and naphthalene. In some cases, the carburizing gas may also contain at least one of CO$_2$, CO, H$_2$, H$_2$O and inert diluents. Alternatively, the carburizing gas may be a mixture of hydrogen and at least one of CO and CO$_2$. Moreover, it may be desirable to contact the catalyst sequentially with a plurality of different carburizing gases, each comprising a hydrocarbon selected from methane, ethane, propane, butane, isobutene, hexane, benzene and naphthalene or a mixture of hydrogen and at least one of CO and CO$_2$.

To avoid damage to the catalyst, the carburization process is controlled so that the maximum temperature in the catalyst treatment zone is less than the maximum temperature in the dehydrocyclization reaction zone, although typically the maximum carburization temperature is higher than the maximum temperature reached in the regeneration zone. Generally the maximum temperature in the catalyst treatment zone is from about 400° C. to about 1100° C., such as from about 500° C. to about 900° C., with the minimum temperature being between 300° C. and 500° C. Typically, the catalyst treatment zone is operated at pressures between 10 and 100 psia (69 and 690 kPa), such as between 15 and 60 psia (103 and 414 kPa). Generally, the average residence time of catalyst particles in the catalyst treatment zone will be between 0.1 and 100 minutes, for example between 1 and 20 minutes. Under these conditions, the carburizing gas reacts with metal oxide species on the catalyst to return the metal to its catalytically active elemental or carbidic form. In addition, the carburizing gas can react with active surface sites on the catalyst support to decrease their tendency to generate coke in the dehydroaromatization reaction zone.

To maintain the temperature required for carburization of the regenerated catalyst, heat can be supplied to the catalyst and/or the carburizing gas prior to or during the carburization step. For example heat can be supplied to the catalyst by indirect heating, by contacting with hot flue gas from the reaction zone or the heating zone, by contacting with the hot gaseous effluent from the carburization process, or by mixing with heated catalyst from the heating zone. Heat is conveniently supplied to the carburization gas by means of an external furnace or heat exchanger or by with heated catalyst from the heating zone.

The catalyst treatment zone may be operated as a fluidized bed reactor, ebulating bed reactor, settling bed reactor, riser reactor or circulating riser reactor. In one embodiment, the catalyst treatment zone comprises a settling bed reactor. Alternatively, the catalyst treatment zone comprises a single fluidized bed reactor with internal baffles to prevent backmixing or a plurality of fluidized bed reactors in series with the regenerated catalyst being cascaded between adjacent reactors. In any event, contact in the catalyst treatment zone is facilitated by arranging that the regenerated catalyst and the carburizing gas flow in opposite directions in said catalyst treatment zone. Employing such a countercurrent flow, a temperature profile may be developed in the catalyst treatment zone such that carburization of the regenerated catalyst initially occurs at a low temperature but the carburization temperature increases as the catalyst flows through the bed.

In some cases, it may be desirable that the heated unregenerated catalyst is initially contacted with a $H_2$-rich stream to partially or fully reduce the metal component of the catalyst prior to the carburization step. It may also be desirable to subject the carburized catalyst to post treatment with $H_2$ and/or $CO_2$ to strip off any excess carbon that may have been deposited on the catalyst by the carburization step.

In practice, as the dehydrocyclization reaction proceeds, fresh dehydrocyclization catalyst will be added to the process either to make up for catalyst lost by mechanical attrition or deactivation and, although there are multiple means of addition of fresh catalyst, to avoid damage to the catalyst, it is generally desirable to add fresh catalyst to a region of the process that is operating at a temperature below the maximum temperature in each dehydrocyclization reaction zone. In one embodiment, fresh dehydrocyclization catalyst is added to the process by introduction into the catalyst treatment zone, whereby the fresh catalyst is contacted with the carburizing gas prior to transfer to the reaction zone for contact with the methane-containing feed. In another, embodiment the catalyst may be added to the lower temperature regions of a reactor system with an inverse temperature profile.

Hydrogen Management

Since hydrogen is a major component of the dehydrocyclization effluent, after recovery of the aromatic products, the effluent is subjected to a hydrogen rejection step to reduce the hydrogen content of the effluent before the unreacted methane is recycled to the dehydrocyclization step and to maximize feed utilization. Typically the hydrogen rejection step comprises reacting at least part of the hydrogen in the dehydrocyclization effluent with an oxygen-containing species, such as CO and/or $CO_2$, to produce water and a second effluent stream having a reduced hydrogen content compared with the first (dehydrocyclization) effluent stream. Suitable hydrogen rejection processes are described below and in our copending PCT Application Serial No. PCT/US2005/044042, filed on Dec. 2, 2005.

Conveniently, the hydrogen rejection step includes (i) methanation and/or ethanation, (ii) a Fischer-Tropsch process, (iii) synthesis of $C_1$ to $C_3$ alcohols, particularly methanol, and other oxygenates, (iv) synthesis of light olefins, paraffins and/or aromatics by way of a methanol or dimethyl ether intermediate and/or (v) selective hydrogen combustion. These steps may be employed sequentially to gain the greatest benefit; for example Fischer-Tropsch may first be employed to yield a $C_2$+ enriched stream followed by methanation to achieve high conversion of the $H_2$.

Typically, as described below, the hydrogen rejection step will generate hydrocarbons, in which case, after separation of the co-produced water, at least a portion of the hydrocarbons is conveniently recycled to the dehydrocyclization step. For example, where the hydrocarbons produced in the hydrogen rejection step comprise paraffins and olefins, the portion recycled to the dehydrocyclization step conveniently comprises, paraffins or olefins with 6 or less carbon atoms, such as 5 or less carbon atoms, for example 4 or less carbon atoms or 3 or less carbon atoms. Where, the hydrocarbons produced in the hydrogen rejection step comprise aromatics, the portion recycled to the dehydrocyclization step conveniently comprises single ring aromatic species.

Methanation/Ethanation

In one embodiment the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrow CH_4 + 2H_2O \qquad \text{(Reaction 7)}$$

$$2CO_2 + 7H_2 \leftrightarrow C_2H_6 + 4H_2O \qquad \text{(Reaction 8)}$$

The carbon dioxide employed is conveniently part of a natural gas stream and typically the same natural gas stream used as the feed to the dehydrocyclization step. Where the carbon dioxide is part of a methane-containing stream, the $CO_2$:$CH_4$ of the stream is conveniently maintained between about 1:1 and about 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2$:$CO_2$ molar ratio close to the stoichiometric proportions required for the desired Reaction 7 or Reaction 8, although small variations can be made in the stoichiometric ratio if it is desired to produce a $CO_2$-containing or $H_2$-containing second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of about 100° C. to about 900° C., such as about 150° C. to about 500° C., for example about 200° C. to about 400° C., a pressure of about 200 kPa to about 20,000 kPa, such as about 500 to about 5000 kPa and a weight hourly space velocity of about 0.1 to about 10,000 hr$^{-1}$, such as about 1 to about 1,000 hr$^{-1}$. $CO_2$ conversion levels are typically between 20 and 100% and conveniently greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2:CO_2$ molar ratio, methane, ethane and higher alkanes, together with some unsaturated $C_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the hydrogen rejection step comprises reaction of at least part of the hydrogen in the dehydrocyclization effluent with carbon monoxide according to the Fischer-Tropsch process to produce $C_2$ to $C_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of about 0.5:1 to about 4:1, such as about 1.5:1 to about 2.5:1, at a temperature of about 175° C. to about 400° C., such as about 180° C. to about 240° C. and a pressure of about 1 to about 100 bar (100 to 10,000 kPa), such as about 10 to about 40 bar (1,000 to 4,000 kPa), in the presence of a Fischer-Tropsch catalyst, generally a supported or unsupported Group VIII, non-noble metal, e.g., Fe, Ni, Ru, Co, with or without a promoter, e.g. ruthenium, rhenium, hafnium, zirconium, titanium. Supports, when used, can be refractory metal oxides such as Group IVB, i.e., titania, zirconia, or silica, alumina, or silica-alumina. In one embodiment, the catalyst comprises a non-shifting catalyst, e.g., cobalt or ruthenium, especially cobalt, with rhenium or zirconium as a promoter, especially cobalt and rhenium supported on silica or titania, generally titania.

In another embodiment, the hydrocarbon synthesis catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of $Cr_2O_3$— ZnO and ZSM-5 Catalysts for the Transformation of Syngas into Liquid Hydrocarbons* by Jose Erena; Ind. Eng. Chem Res. 1998, 37, 1211-1219, incorporated herein by reference.

The Fischer-Tropsch liquids, i.e., $C_5$+, are recovered and light gases, e.g., unreacted hydrogen and CO, $C_1$ to $C_3$ or $C_4$ and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to a shift catalyst whereby carbon monoxide is produced by the reverse water gas shift reaction:

$$CO_2 + H_2 \leftrightarrow CO + H_2O \qquad \text{(Reaction 9)}$$

and by the following reaction:

$$CH_4 + H_2O \leftrightarrow CO + 3H_2 \qquad \text{(Reaction 10)}$$

Alcohol Synthesis

In a further embodiment the hydrogen rejection step comprises reaction of at least part of the hydrogen in the dehydrocyclization effluent with carbon monoxide to produce $C_1$ to $C_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen ($H_2$) to carbon oxides ($CO+CO_2$) in the range of from about 0.5:1 to about 20:1, such as in the range of from about 2:1 to about 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa to about 12,500 kPa, such as from about 2,000 kPa to about 10,000 kPa, for example 2,500 kPa to about 7,500 kPa. Gas hourly space velocities vary depending upon the type of process that is used, but generally the gas hourly space velocity of flow of gas through the catalyst bed is in the range of from about 50 hr$^{-1}$ to about 50,000 hr$^{-1}$, such as from about 250 hr$^{-1}$ to about 25,000 hr$^{-1}$, for example from about 500 hr$^{-1}$ to about 10,000 hr$^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Selective Hydrogen Combustion

In yet another embodiment, the hydrogen rejection step comprises selective hydrogen combustion, which is a process in which hydrogen in a mixed stream is reacted with oxygen to form water or steam without substantially reacting hydrocarbons in the stream with oxygen to form carbon monoxide, carbon dioxide, and/or oxygenated hydrocarbons. Generally, selective hydrogen combustion is carried out in the presence of an oxygen-containing solid material, such as a mixed metal oxide, that will release a portion of the bound oxygen to the hydrogen.

One suitable selective hydrogen combustion process is described in U.S. Pat. No. 5,430,210, incorporated herein by reference, and comprises contacting at reactive conditions a first stream comprising hydrocarbon and hydrogen and a second stream comprising oxygen with separate surfaces of a membrane impervious to non-oxygen containing gases, wherein said membrane comprises a metal oxide selective for hydrogen combustion, and recovering selective hydrogen combustion product. The metal oxide is typically a mixed metal oxide of bismuth, indium, antimony, thallium and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the hydrogen formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of hydrogen. The equilibrium dehydrogenation catalyst may comprise platinum and the selective metal oxide combustion catalyst may contain bismuth, antimony, indium, zinc, thallium, lead and tellurium or a mixture thereof.

U.S. Patent Application Publication No. 2004/0152586, published Aug. 5, 2004 and incorporated herein by reference, describes a process for reducing the hydrogen content of the effluent from a cracking reactor. The process employs a catalyst system comprising (1) at least one solid acid cracking component and (2) at least one metal-based selective hydrogen combustion component consisting essentially of (a) a metal combination selected from the group consisting of: i) at least one metal from Group 3 and at least one metal from Groups 4-15 of the Periodic Table of the Elements; ii) at least one metal from Groups 5-15 of the Periodic Table of the Elements, and at least one metal from at least one of Groups 1, 2, and 4 of the Periodic Table of the Elements; iii) at least one metal from Groups 1-2, at least one metal from Group 3, and at least one metal from Groups 4-15 of the Periodic Table of the Elements; and iv) two or more metals from Groups 4-15 of the Periodic Table of the Elements; and (b) at least one of oxygen and sulfur, wherein the at least one of oxygen and sulfur is chemically bound both within and between the metals.

The selective hydrogen combustion reaction of the present invention is generally conducted at a temperature in the range of from about 300° C. to about 850° C. and a pressure in the range of from about 1 atm to about 20 atm (100 to 2000 kPa).

Aromatic Product Recovery/Treatment

In addition to hydrogen, the other major products of the dehydrocyclization step are benzene and naphthalene. These products can be separated from the dehydrocyclization effluent, typically by solvent extraction followed by fractionation, and then sold directly as commodity chemicals. Alternatively, some or all of the benzene and/or naphthalene can be alkylated to produce, for example, toluene, xylenes and alkyl naphthalenes and/or can be subjected to hydrogenation to produce, for example, cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). Suitable alkylation and hydrogenation processes are described below and in more detail in our copending PCT Application Serial Nos. PCT/US2005/043523, No. 2004B156), filed on Dec. 2, 2005 and PCT/US2005/044038, filed on Dec. 2, 2005.

Aromatics Alkylation

Alkylation of aromatic compounds such as benzene and naphthalene is well known in the art and typically involves reaction of an olefin, alcohol or alkyl halide with the aromatic species in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e, those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In one embodiment of the present process, benzene is recovered from the dehydrocyclization effluent and then alkylated with an olefin, such as ethylene produced as a by-product of a hydrogen rejection step employing ethanation/methanation. Typical conditions for carrying out the vapor phase alkylation of benzene with ethylene include a temperature of from about 650 to 900° F. (343 to 482° C.), a pressure of about atmospheric to about 3000 psig (100 to 20,800 kPa), a WHSV based on ethylene of from about 0.5 to about 2.0 hr$^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa), a WHSV based on ethylene of from about 0.1 to about 20 hr$^{-1}$ and a mole ratio of benzene to ethylene of from 1:1 to 30:1.

Conveniently, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In another embodiment of the present process, the alkylating agent is methanol or dimethylether (DME) and is used to alkylate benzene and/or naphthalene recovered from the dehydrocyclization effluent to produce toluene, xylenes, methylnaphthalenes and/or dimethylnaphthalenes. Where the methanol or DME is used to alkylate benzene, this is conveniently effected in the presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2 dimethylbutane of about 0.1-15 sec$^{-1}$ when measured at a temperature of 120° C. and a 2,2 dimethylbutane pressure of 60 torr (8 kPa). Such a process is selective to the production of para-xylene and is described in, for example, U.S. Pat. No. 6,504,272, incorporated herein by reference. Where the methanol is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847 and 5,001,295, incorporated herein by reference.

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reactions 5 and 8 above.

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn on alumina, silica or titania, and is operated under conditions including a temperature of about 500° C. to about 1200° C., such as about 600° C. to about 1000° C., for example about 700° C. to about 950° C. and a pressure of about 1 kPa to about 10,000 kPa, such as about 2,000 kPa to about 10,000 kPa, for example about 3000 kPa to about 5,000 kPa. Gas hourly space velocities may vary depending upon the type of process used, but generally the gas hourly space velocity of flow of gas through the catalyst bed is in the range of about 50 hr$^{-1}$ to about 50,000 hr$^{-1}$, such as about 250 hr$^{-1}$ to about 25,000 hr$^{-1}$, more for example about 500 hr$^{-1}$ to about 10,000 hr$^{-1}$.

The effluent from the reverse shift reactor can then be fed to an alkylation reactor operating under conditions to cause reactions such as the following to occur:

   (Reaction 11)

   (Reaction 12)

   (Reaction 13)

Suitable conditions for such an alkylation reactor would include a temperature of about 100 to about 700° C., a pressure of about 1 to about 300 atmospheres (100 to 30,000 kPa), and a WHSV for the aromatic hydrocarbon of about 0.01 to about 100 hr$^{-1}$. A suitable catalyst would comprise a molecular sieve having a constraint index of 1 to 12, such as ZSM-5, typically together with one or metals or metal oxides, such as copper, chromium and/or zinc oxide.

Conveniently, where the alkylation catalyst includes a molecular sieve, the latter is modified to change its diffusion characteristics such that the predominant xylene isomer produced by Reaction 11 is paraxylene. Suitable means of diffusion modification include steaming and ex-situ or in-situ deposition of silicon compounds, coke, metal oxides, such as MgO, and/or P on the surface or in the pore mouths of the molecular sieve. Also preferred is that an active metal be incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the hydrogen and other low molecular weight materials, conveniently by solvent extraction. The aromatics products could then be fractionated into a benzene fraction, a toluene fraction, a $C_8$ fraction and a heavy fraction containing naphthalene and alkylated naphthalenes. The $C_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as saleable product, recycled to the alkylation reactor or fed to a toluene disproportionation unit, such as a selective toluene disproportionation unit for the preparation of additional p-xylene.

Aromatics Hydrogenation

In addition to or instead of the alkylation step, at least part of the aromatic components in the dehydrocyclization effluent can be hydrogenated to generate useful products such as cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). These products can be employed as fuels and chemical intermediates and, in the case of tetralin and decalin, can be used as the solvent for extracting the aromatic components from the dehydrocyclization effluent.

The hydrogenation is conveniently, but not necessarily, conducted after separation of the aromatic components from the dehydrocyclization effluent and conveniently employs part of the hydrogen generated by the dehydrocyclization reaction. Suitable aromatic hydrogenation processes are well known in the art and typically employ a catalyst comprising Ni, Pd, Pt, Ni/Mo or sulfided Ni/Mo supported on alumina or silica support. Suitable operating conditions for the hydrogenation process include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 hr$^{-1}$, such as about 2 to about 10 hr$^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as $La_2O_3$—ZnO. Homogeneous noble metal catalyst systems can also be used. Examples of partial hydrogenation processes are disclosed in U.S. Pat. Nos. 4,678,861; 4,734,536; 5,457,251; 5,656,761; 5,969,202; and 5,973,218, the entire contents of which are incorporated herein by reference.

An alternative hydrogenation process involves low pressure hydrocracking of the naphthalene component to produce alkylbenzenes over a catalyst such as sulfided Ni/W or sulfided Ni supported on an amorphous aluminosilicate or a zeolite, such as zeolite X, zeolite Y or zeolite beta. Suitable operating conditions for low pressure hydrocracking include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 hr$^{-1}$, such as about 2 to about 10 hr$^{-1}$.

The invention will now be more particularly described with reference to the accompanying drawings and the following non-limiting Examples.

EXAMPLE 1

Figure 1B:
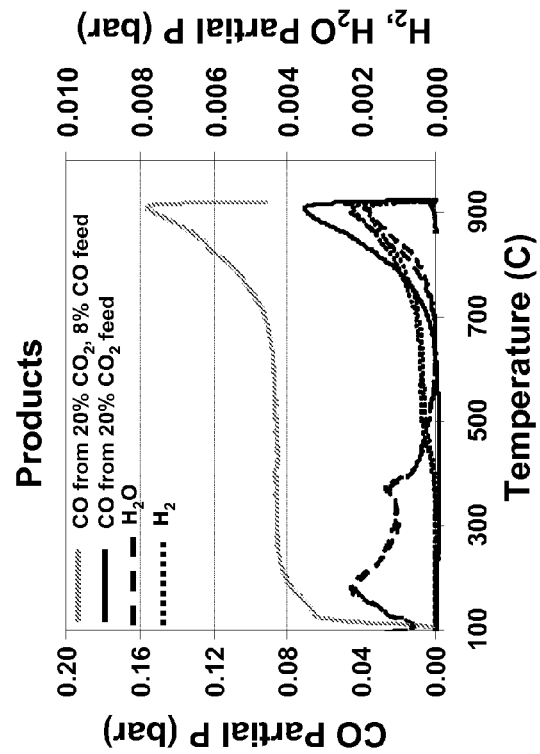

Separate samples of a coked Mo/ZSM-5 catalyst (having a Si/Al$_2$ ratio of 25:1 and a Mo loading of 7.5 wt % and a coke level of 12.4 wt %) were heated from 100° C. to about 925° C. in (a) a helium atmosphere containing 20 mol % carbon dioxide and (b) a helium atmosphere containing 20 mol % carbon dioxide and 8 mol % carbon monoxide. The composition of the feed in each test is shown in FIG. 1(a) and the composition of the product in each test is shown in FIG. 1(b) and Table 1.

TABLE 1

| | Amount of compound generated at T > 600° C. (mmol/g catalyst) | |
|---|---|---|
| Compound | 20% CO$_2$/He | 20% CO$_2$/8% CO/He |
| CO$_2$[1] | 8.7 | 8.5 |
| CO | 17.9 | 16.9 |
| H$_2$ | 0.45 | 0.59 |
| H$_2$O | 0.48 | 0.41 |

[1]CO$_2$ consumed—all other species generated.

It will be seen that the amount of CO detected in each test was equal to about twice the amount of CO$_2$ consumed.

EXAMPLE 2

A 300 mg Mo/ZSM-5 catalyst aliquot (having a Si/Al$_2$ ratio of 25:1 and a Mo loading of 7.5 wt %) diluted with 750 mg quartz was subjected to the following activation, methane dehydrocyclization and regeneration cycles:

Activation (a) Heat catalyst in 75 sccm He at 5° C./minute to 500° C. and hold for 6 hours at a He pressure of 24 psia (165 kPaa);
(b) Cool to 125° C. in He;
(c) Carburize Mo by heating catalyst with 75 sccm of 85 mol % H$_2$/15 mol % CH$_4$ mixture at 5° C./minute to 800° C. and then holding for 0.5 hour at 24 psia (165 kPaa);
(d) Cool to 785° C. in H$_2$/CH$_4$ mixture;
(e) Initiate dehydrocyclization reaction.

Dehydrocyclization (a) Supply hydrocarbon feed (75.2% CH$_4$, 12.9% H$_2$, 9.99% Ar, 1.73% CO and 0.21% C$_2$H$_4$, all by mol %) at 49 sccm and 785° C. for 4 minutes;
(b) Initiate H$_2$ or CO$_x$ regeneration cycle.

H$_2$ Regeneration (a) After dehydrocyclization cycle, optionally purge with 75 sccm He at 785° C. for 5 minutes;
(b) Switch to 75 sccm H$_2$, ramp at 5° C./minute to 875° C. and hold for 24 minutes at a H$_2$ pressure of 50 psia (345 kPaa);
(c) Optionally purge for 5 minutes with 75 sccm He while reactor cools to 785° C.;
(d) Initiate dehydrocyclization cycle.

CO$_x$ Regeneration (a) After dehydrocyclization cycle, purge with 75 sccm He for 15 minutes while reactor cools to 750° C.;
(b) Switch to 75 sccm of 1.2% CO$_2$, 2.8% CO (a CO to CO$_2$ partial pressure ratio of 2.3:1), 96% He (all mol %) at a total pressure of 40 psia (276 kPaa) and CO$_2$ partial pressure of 0.5 psia (3.45 kPaa) for 1 minute;
(c) Purge for 10 minutes with 75 sccm He and ramp temperature at 5° C./minute in He to 785° C. Continue He purge until total purge time is 15 minutes.
(d) Initiate dehydrocyclization cycle.

In the test, after activation, the catalyst was subjected to alternating dehydrocyclization and H$_2$ regeneration cycles for 10 cycles until, after the eleventh dehydrocyclization cycle, the catalyst was subjected to a CO$_x$ regeneration cycle. This was repeated for a total of 67 dehydrocyclization cycles. In each case, performance was significantly higher following the CO$_x$ regeneration and remained stable for the ensuing 10 H$_2$ regenerations.

After 67 dehydrocyclization cycles, the protocol was changed to use 2 CO$_x$ regeneration cycles after each 10 H$_2$ regenerations. The number of CO$_x$ regeneration cycles after each 10 H$_2$ regenerations was increased to two and performance was still stable but declined somewhat after the two CO$_x$ regeneration cycles and five H$_2$ regeneration cycles. Subsequently, the number of CO$_x$ regeneration cycles after each five H$_2$ regenerations was increased to four but resulted in further loss in catalyst performance.

Figure 2:
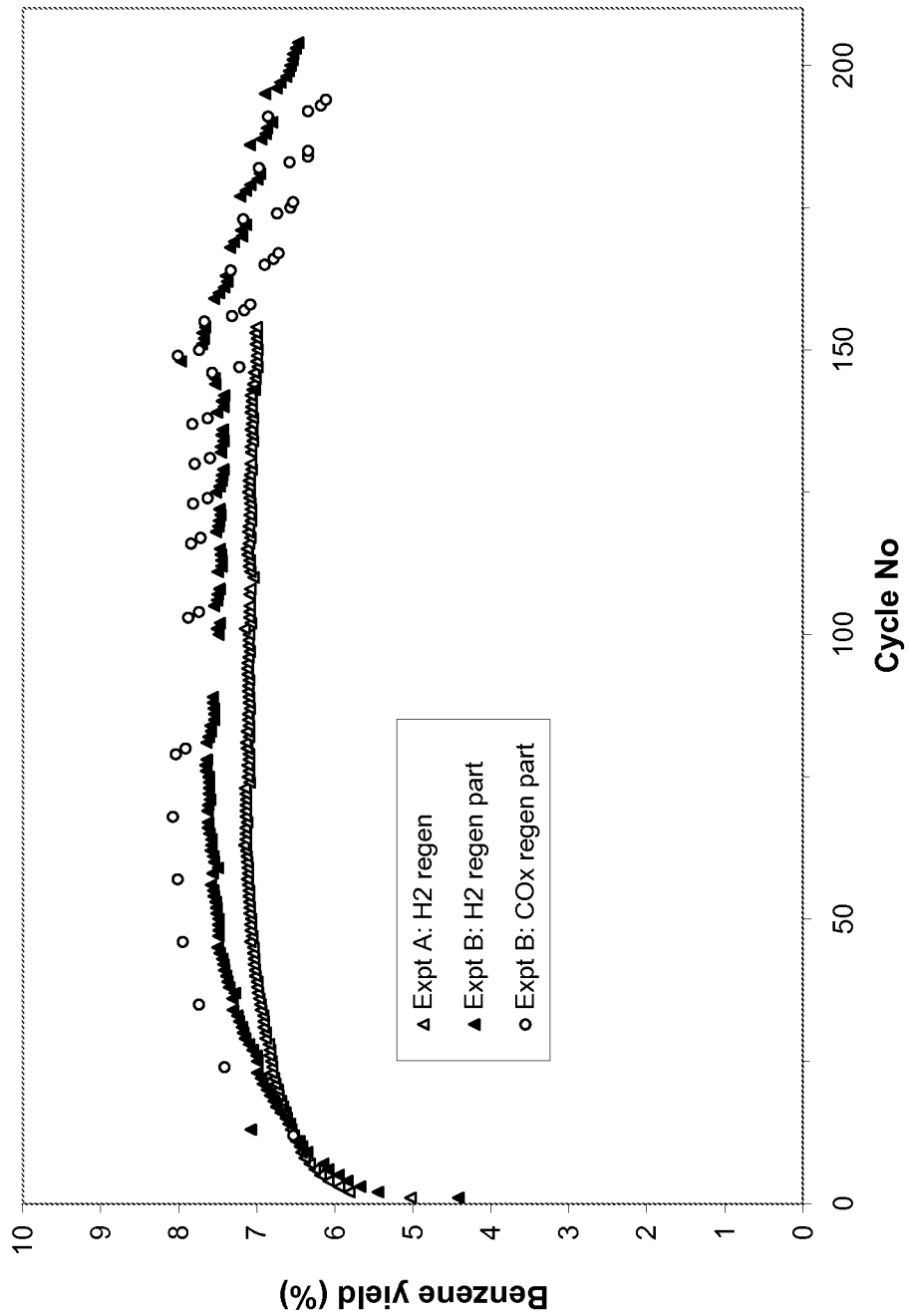
FIG. 2 is a graph of benzene yield against cycle number in the methane dehydrocyclization process of Example 2.

The results are summarized in FIG. 2 and Table 2.

TABLE 2

| No. reaction cycles | Regen gas | Regen time (mins) | Coke after regen (wt %) | Comments |
|---|---|---|---|---|
| 87 | He | 1 | 9.35 | 750° C., 40 psia |
| 154 | H$_2$ | 24 | Est. 4.64 | 875° C., 50 psia |
| 111 | CO$_x$ | 1 | 7.91 | 750° C., 40 psia (P$_{CO2}$ = 0.5 psia) |
| 173 | CO$_x$ | 4 | 5.34 | 875° C., 24 psia (P$_{CO2}$ = 7 psia) |
| 204 | H$_2$/COx (Expt. B in FIG. 2) | 24/1 | 3.38 | 750° C., 40 psia (P$_{CO2}$ = 0.5 psia) |

EXAMPLE 3

300 mg Mo/ZSM-5 catalyst aliquots (having a Si/Al$_2$ ratio of 25:1 and a Mo loading of 7.5 wt %) diluted with 750 mg quartz were subjected to alternating methane dehydrocyclization and CO$_x$ regeneration cycles as described in Table 3 below.

TABLE 3

| Expt No | Temp for CO$_x$ regen (° C.) | Time for CO$_x$ regen (min) | P$_{total}$ (psia)* | P$_{COx}$ (psia) | Partial pressure CO$_2$ (psia) | Partial pressure CO (psia) | Ratio: CO to CO$_2$ |
|---|---|---|---|---|---|---|---|
| 1 | 750 | 1 | 23 | 10 | 2.3 | 7.7 | 3.3 |
| 2 | 750 | 1 | 20 | 20 | 6.0 | 14.0 | 2.3 |
| 3 | 925 | 1 | 23 | 10 | 0.9 | 9.1 | 10.1 |
| 4 | 925 | 1 | 61 | 40 | 3.6 | 36.4 | 10.1 |
| 5 | 750 | 4 | 23 | 10 | 3.0 | 7.0 | 2.3 |
| 6 | 750 | 4 | 23 | 10 | 0.9 | 9.1 | 10.1 |
| 7 | 750 | 20 | 23 | 10 | 0.9 | 9.1 | 10.1 |
| 8 | 750 | 1 | 23 | 10 | 0.9 | 9.1 | 10.1 |
| 9 | 750 | 4 | 23 | 3 | 0.3 | 2.7 | 9.0 |

TABLE 3-continued

| Expt No | Temp for $CO_x$ regen (° C.) | Time for $CO_x$ regen (min) | $P_{total}$ (psia)* | $P_{CO_x}$ (psia) | Partial pressure $CO_2$ (psia) | Partial pressure CO (psia) | Ratio: CO to $CO_2$ |
|---|---|---|---|---|---|---|---|
| 10 | 750 | 4 | 20 | 20 | 9.0 | 11.0 | 1.2 |
| 11 | 750 | 4 | 40 | 40 | 18.0 | 22.0 | 1.2 |
| 12 | 925 | 4 | 23 | 10 | 0.9 | 9.1 | 10.1 |
| 13 | 750 | 1 | 40 | 40 | 18.0 | 22.0 | 1.2 |
| 14 | 700 | 4 | 23 | 10 | 4.5 | 5.5 | 1.2 |
| 15 | 700 | 12 | 23 | 10 | 4.5 | 5.5 | 1.2 |
| 16 | 700 | 12 | 23 | 10 | 3.0 | 7.0 | 2.3 |

*Includes dilution with He gas when applicable.

Figure 3A:
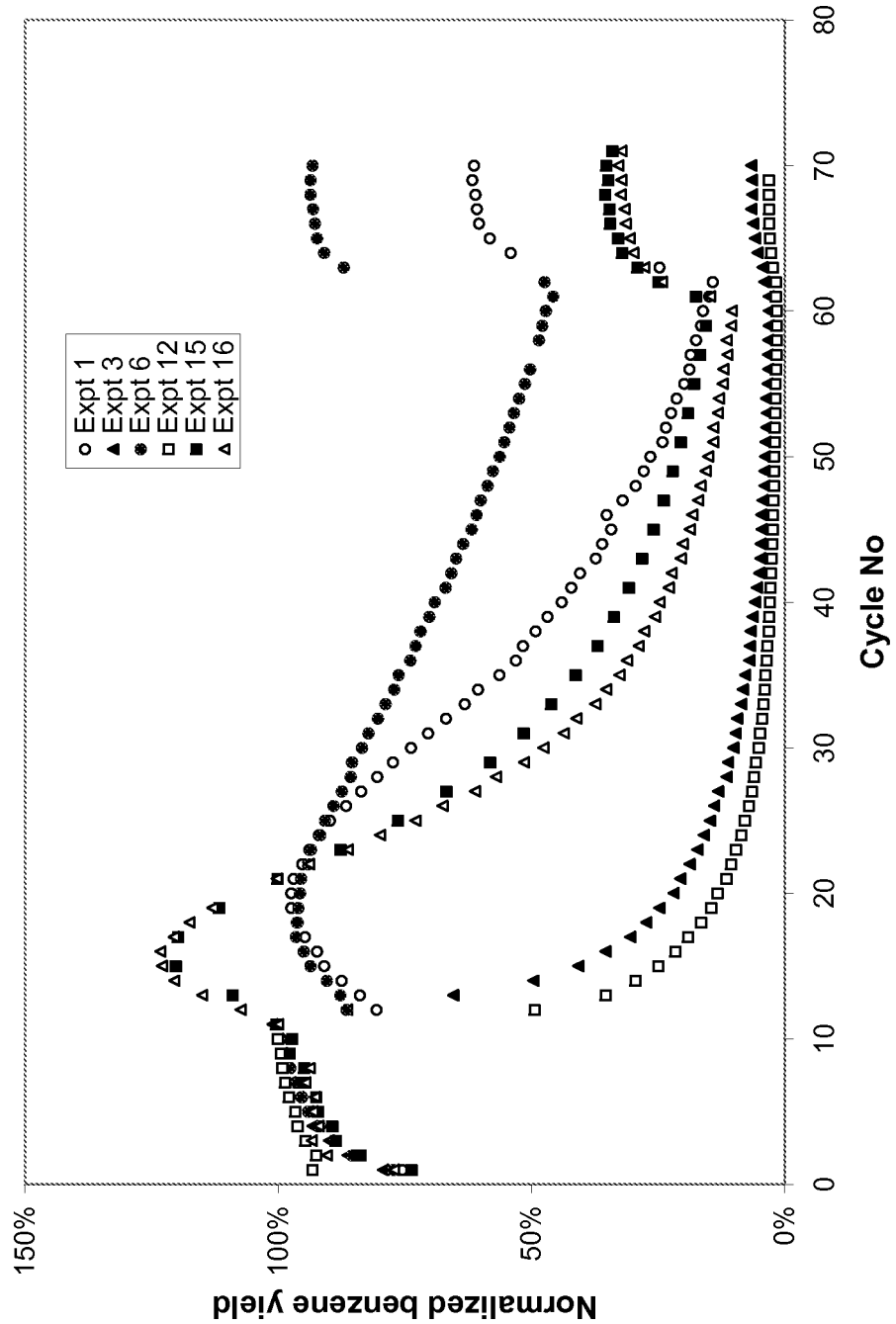
FIGS. 3(a) to (d) and FIG. 4 are graphs of normalized benzene yield (with respect to benzene yield at cycle 11) against cycle number in the methane dehydrocyclization process of Example 3.

The results summarized in FIG. 3a-d demonstrate the following:
$CO_x$ regeneration at 925° C. caused rapid deactivation and permanent damage of the catalyst of Example 3. FIG. 3a shows dramatically higher recovery after $H_2$ regeneration for Expt. 6 and Expt. 1 (750° C.) as compared with Expt. 12 and Expt. 3 (925° C.)

$CO_x$ regeneration at 700° C., also in FIG. 3a, (Expt. 15 and Expt. 16) did not efficiently remove coke from the catalyst of Example 3 and seemed to damage the catalyst in that catalyst activity could only be partially recovered by $H_2$ regeneration.

Using the catalyst and conditions tested, $CO_x$ regeneration at 750° C. seemed to produce the best results.

Figure 3B:
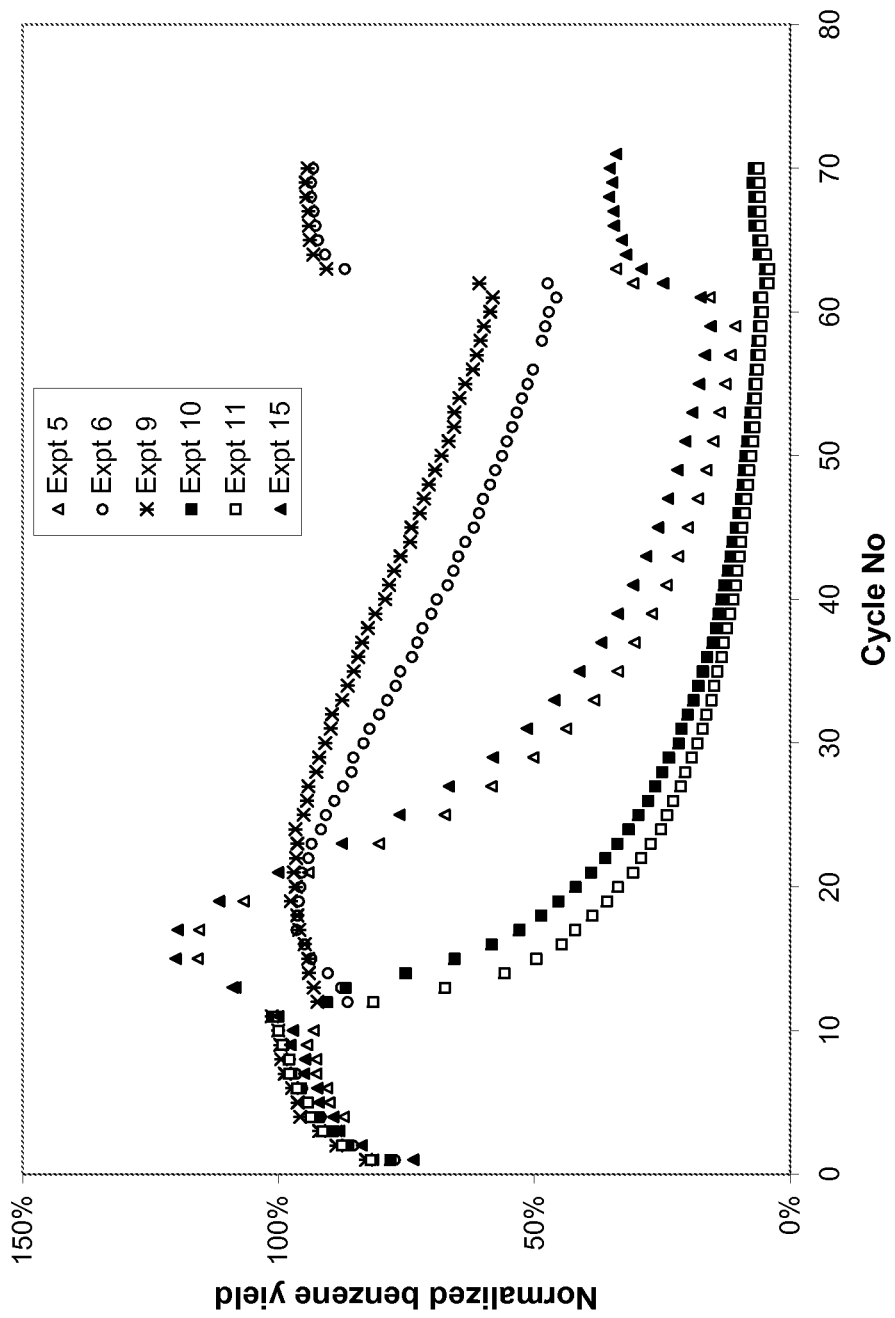

The results in FIG. 3b show that at high $CO_2$ partial pressure (Expt. 11 at 18 psia CO2, Expt. 10 at 9 psia $CO_2$) performance declines rapidly and recovery after $H_2$ regeneration (after cycle 61) is less than at low $CO_2$ partial pressure, such as those observed in Expt. 5 at 3 psia $CO_2$, Expt. 6 at 0.9 psia $CO_2$, Expt. 9 at 0.3 psia $CO_2$.

Figure 3C:
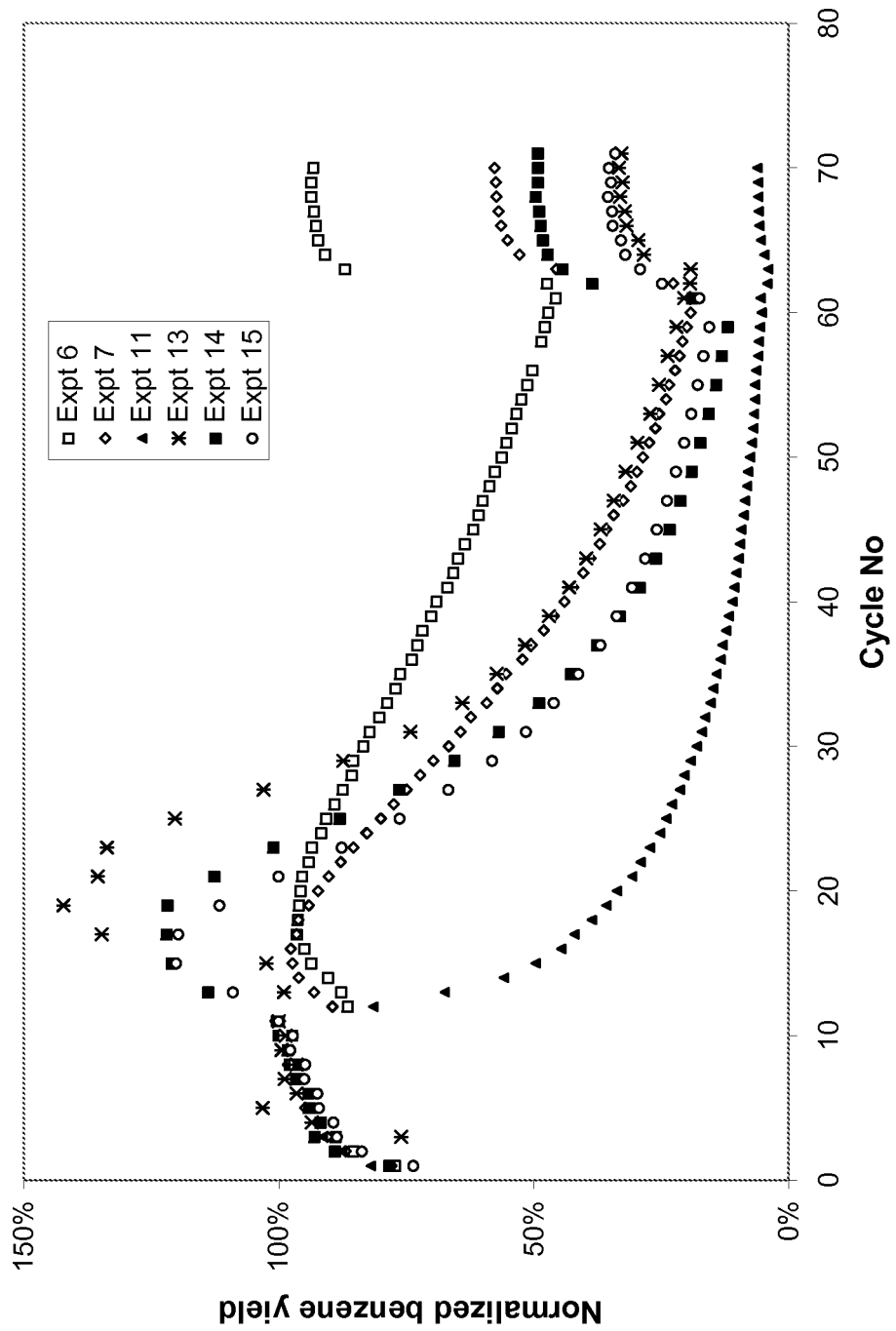

FIG. 3c also shows that shorter regeneration time [Expt. 6 (1 min) as compared with Expt. 7 (20 min)] results in better performance recovery after $H_2$ regeneration after Cycle 61 at low $CO_2$ partial pressures (0.9 psia). This effect is even more pronounced at higher $CO_2$ partial pressures [at 18 psia for Expt. 13 (1 min) as compared with Expt. 11 (4 min) and at 4.5 psi for Expt. 14 (4 min) and Expt. 15 (12 min)].

Figure 3D:
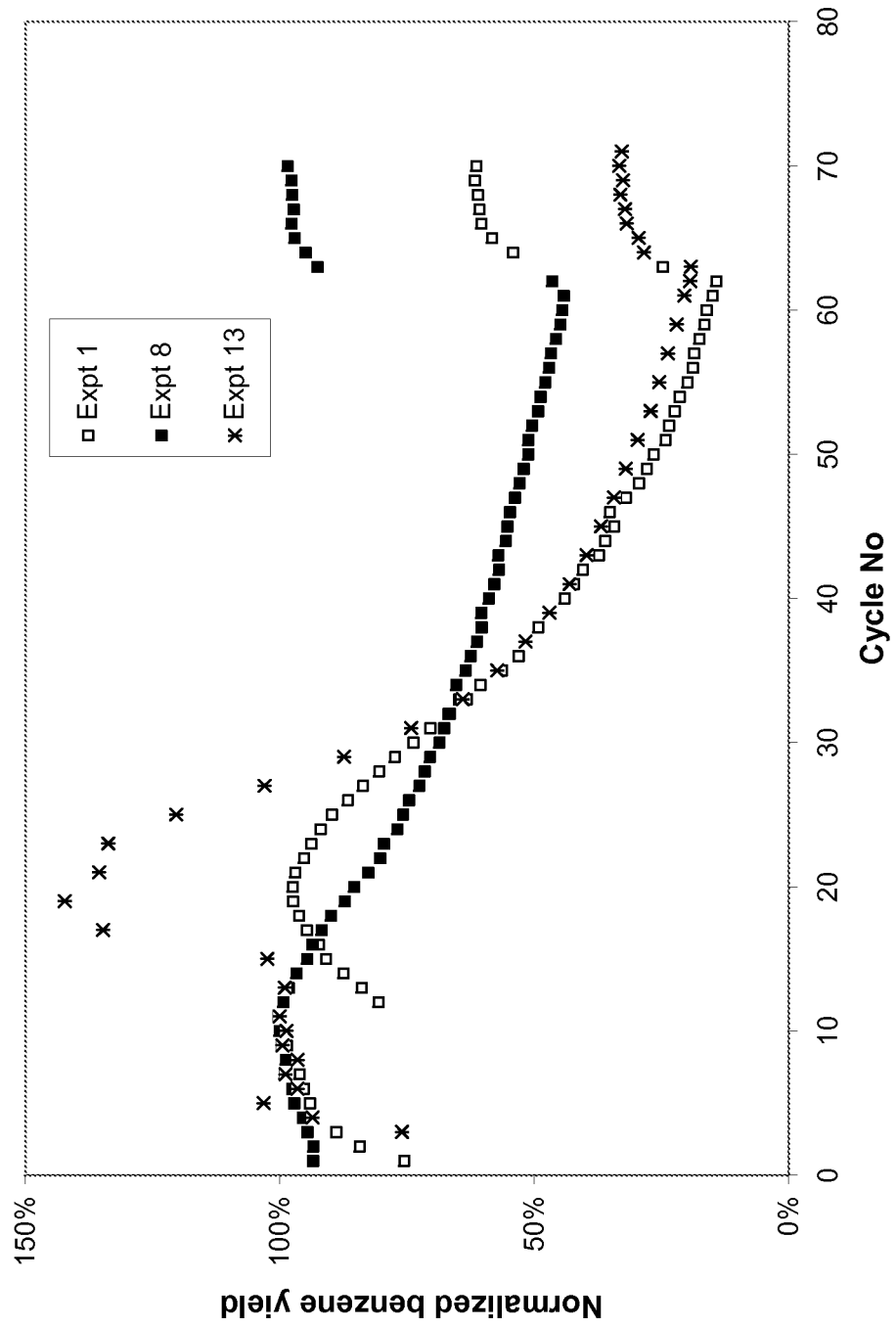
Figure 4:
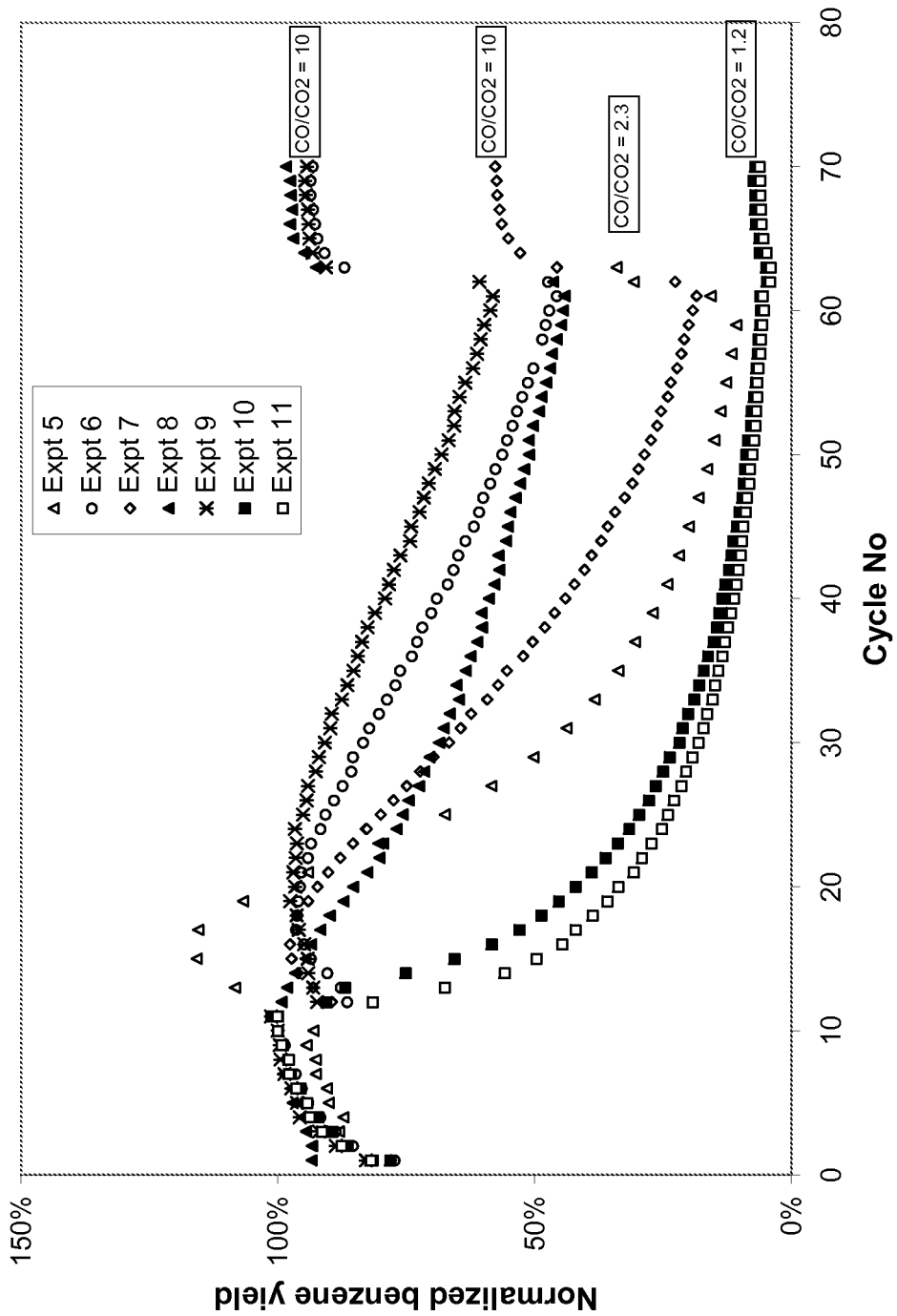

With the catalyst of Example 3 and effecting $CO_x$ regeneration at 750° C. for 1 minute, the recovery after $H_2$ regeneration seemed to improve with lower $CO_2$ partial pressures as shown in FIG. 3d [e.g., Expt. 8 (0.9 psia $CO_2$-best) as compared with Expt. 1 (2.3 psia $CO_2$-good) and Expt. 13 (18 psia $CO_2$-poor)] and higher $CO/CO_2$ ratios as shown in FIG. 4.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for the regeneration of a coked metal-containing catalyst, the process comprising the steps of:
   (i) contacting the coked metal-containing catalyst in a regeneration zone with an atmosphere consisting of carbon dioxide, carbon monoxide, and less than 100 ppm of molecular oxygen, wherein the carbon monoxide and the carbon dioxide have a ratio of partial pressures in the regeneration zone where the ratio of the partial pressure of the carbon monoxide to the partial pressure of the carbon dioxide in the regeneration zone is at least 2.3:1, and wherein the partial pressure of carbon dioxide in the regeneration zone is between about 0.1 and about 40 psia, at a temperature of at least 400° C.; and
   (ii) contacting the coked metal-containing catalyst in a regeneration zone with an atmosphere which contains hydrogen at a temperature of at least 400° C. consecutively with said contacting with said atmosphere consisting of carbon dioxide, carbon monoxide, and less than 100 ppm of molecular oxygen, so as to remove at least part of the carbonaceous material on the coked metal-containing catalyst and regenerate said catalyst.

2. The process according to claim 1, wherein said atmosphere in said step (i) consists of less than 10 ppm of molecular oxygen.

3. The process according to claim 1, wherein the ratio of the partial pressure of carbon monoxide to partial pressure of carbon dioxide in the regeneration zone in said step (i) is between about 2.3:1 and about 100:1.

4. The process according to claim 1, wherein the partial pressure of carbon dioxide in the regeneration zone in said step (i) is less than or equal to 40 psia.

5. The process according to claim 1, wherein the partial pressure of carbon dioxide in the regeneration zone in said step (i) is between about 0.1 and about 3 psia.

6. The process according to claim 1, wherein said contacting in said step (i) is for a time of less than 120 minutes.

7. The process according to claim 1, wherein said contacting in said step (i) is for a time between about 0.1 and about 60 minutes.

8. The process according to claim 1, wherein said temperature in said step (i) is between about 400° C. and about 1200° C.

9. The process according to claim 1, wherein said temperature in said step (i) is between about 600° C. and about 900° C.

10. The process according to claim 1, wherein said atmosphere in said step (i) comprises less than 1 ppm $O_2$.

11. The process according to claim 1, wherein the metal of said coked metal-containing catalyst is selected from molybdenum, tungsten, cobalt, zinc, rhenium, platinum, palladium and mixtures thereof.

12. The process according to claim 1, wherein the metal of said coked metal-containing catalyst comprises molybdenum in a carbide form.

13. The process according to claim 1, wherein said coked metal-containing catalyst comprises a support selected from ZSM-5, silica, alumina, zirconia, titania, barium aluminate and mixtures thereof.

14. The process according to claim 1, the process further comprising:
   (a) supplying a feedstock comprising methane to a reaction zone comprising a metal-containing catalyst;
   (b) operating said reaction zone under reaction conditions effective to convert at least a portion of said methane to higher hydrocarbons and to deposit carbonaceous material on the metal-containing catalyst causing deactivation of the catalyst;
   (c) transferring at least a portion of said deactivated metal-containing catalyst to a regeneration zone;
   (d) contacting said portion of said deactivated metal-containing catalyst in said regeneration zone with an atmosphere consisting of carbon dioxide, carbon monoxide, and less than 100 ppm of molecular oxygen, wherein the ratio of the partial pressure of carbon monoxide to the partial pressure of carbon dioxide in the regeneration zone is at least 2.3:1, at a temperature of at least 400° C., so as to remove at least part of the carbonaceous material on the metal-containing catalyst and regenerate said catalyst;
- (e) returning at least part of the catalyst regenerated in (d) to said reaction zone; and
- (f) contacting at least a portion of said deactivated metal-containing catalyst in a regeneration zone with an atmosphere which contains hydrogen at a temperature of at least 400° C. so as to remove at least part of the carbonaceous material on the metal-containing catalyst and regenerate said catalyst.

15. The process according to claim 14, wherein the ratio of the partial pressure of carbon monoxide to the partial pressure of carbon dioxide in said contacting (d) is at least 10:1.

16. The process according to claim 14, wherein the ratio of the partial pressure of carbon monoxide to the partial pressure of carbon dioxide in said contacting (d) is between about 2.3:1 and about 20:1.

17. The process according to claim 14, wherein said atmosphere in said contacting (d) consists of less than 10 ppm $O_2$, preferably less than 1 ppm $O_2$.

18. The process according to claim 14, wherein the catalyst is cycled between said operating (b) and at least one of said contacting (d) or said contacting (f) such that the catalyst undergoes said contacting (f) about 2 to about 100 times for each time the catalyst undergoes said contacting (d).

19. The process according to claim 1, wherein the ratio of the partial pressure of carbon monoxide to the partial pressure of carbon dioxide is at least 10:1.

* * * * *